United States Patent
Matsuda et al.

(10) Patent No.: US 6,874,379 B2
(45) Date of Patent: Apr. 5, 2005

(54) PIPET DEVICE WITH DISPOSABLE TIP

(75) Inventors: Takeshi Matsuda, Kyoto (JP); Shigeru Kitamura, Kyoto (JP)

(73) Assignee: Arkray, Inc., Kyoto (JP)

(*) Notice: Subject to any disclaimer, the term of this patent is extended or adjusted under 35 U.S.C. 154(b) by 72 days.

(21) Appl. No.: 10/344,914
(22) PCT Filed: Aug. 14, 2001
(86) PCT No.: PCT/JP01/07021
§ 371 (c)(1),
(2), (4) Date: Feb. 18, 2003
(87) PCT Pub. No.: WO02/16039
PCT Pub. Date: Feb. 28, 2002

(65) Prior Publication Data
US 2003/0177849 A1 Sep. 25, 2003

(30) Foreign Application Priority Data
Aug. 18, 2000 (JP) ......................... 2000-248217

(51) Int. Cl.⁷ .............................. B01L 3/02; G01N 1/14
(52) U.S. Cl. ................................. 73/864.14; 73/864.22
(58) Field of Search ..................... 73/864.14–864.16, 73/864.22

(56) References Cited

U.S. PATENT DOCUMENTS

| | | | | |
|---|---|---|---|---|
| 4,072,330 A | * | 2/1978 | Brysch ................. | 73/864.14 |
| 4,593,837 A | | 6/1986 | Jakubowicz et al. . | 73/864.17 X |
| 4,679,446 A | * | 7/1987 | Sheehan et al. ...... | 73/864.14 X |
| 4,863,695 A | * | 9/1989 | Fullemann ........... | 73/864.14 X |
| 5,133,218 A | * | 7/1992 | Uffenhiemer et al. .... | 73/864.14 |
| 5,193,403 A | * | 3/1993 | Burgisser ................ | 73/864.17 |
| 5,734,114 A | | 3/1998 | Itoh ...................... | 73/864.14 |
| 6,415,669 B1 | * | 7/2002 | Carl ...................... | 73/864.14 |
| 6,499,363 B1 | * | 12/2002 | Morimoto et al. .... | 73/864.14 X |
| 6,537,505 B1 | * | 3/2003 | LaBudde et al. ...... | 73/864.14 X |
| 6,749,812 B2 | * | 6/2004 | Cronenberg et al. ...... | 422/100 |

FOREIGN PATENT DOCUMENTS

| | | | | |
|---|---|---|---|---|
| EP | 337726 A2 | * | 10/1989 | ........... 422/100 |
| JP | 6-242129 | | 9/1994 | ....... G01N/35/06 |

* cited by examiner

Primary Examiner—Thomas P. Noland
(74) Attorney, Agent, or Firm—Merchant & Gould P.C.

(57) ABSTRACT

A pipet device (A) includes a pipet nozzle (1) formed with an internal passage (10) and a hollow pipet tip (4) removably attached to the nozzle (1). The tip (4) is movable between a normal fixed position and a completely detached position relative to the nozzle (1). The nozzle (1) is formed with an external-air intake groove (16). The intake groove (16) is closed by the tip (4) when the tip (4) is at the normal fixed position. The intake groove (16) is exposed from the tip (4) when the tip (4) is moved from the normal fixed position toward the completely detached position.

6 Claims, 4 Drawing Sheets

PIPET DEVICE WITH DISPOSABLE TIP

TECHNICAL FIELD

The present invention relates to a pipet device used for measuring or transferring a liquid sample such as blood or urine.

BACKGROUND ART

Conventionally, a pipet device is often used in examining a liquid sample (such as blood or urine). A typical pipet device includes an elongate tube for sucking and retaining a liquid sample. Using such a pipet device, a taken sample is transferred from one container to another container or to an analyzer. (Hereinafter, this work is referred to as "pipetting".)

In handling plural kinds of samples, different kinds of samples should not be mixed by pipetting. Conventionally, therefore, as shown in FIG. 5A, a disposable tip 9 is fitted outwardly to the end of a pipet nozzle 8 so that a sucked sample m does not come into contact with the pipet nozzle 8. When discharging of the sample m is finished, the tip 9 is replaced with a new tip.

However, the above-described prior art method is not sufficient to prevent different kinds of samples from mixing and has the following problems.

In discharging the sample m from the tip 9, it is difficult to completely let out the sample m, and a slight amount of sample m may remain on the inner surface of the tip 9. The remaining sample m may contaminate the pipet nozzle in the following manner. As shown in FIG. 5B, after the sample m is discharged, the tip 9 is pulled out from the pipet nozzle 8 in the arrow N1 direction for replacement. At that time, the volume of a space S within the tip 9 increases, generating a negative pressure in the tip 9. As a result, air flows into the tip 9 through an end opening 90a. The higher the speed in pulling out the tip 9 is, the larger negative pressure is generated in the tip 9, causing air to flow in at a higher speed. Such air flow transfers the sample m remaining in the tip 9 to the pipet nozzle 8, thereby contaminating the pipet nozzle 8.

Such a problem can be solved by making the tip 9 long or by pulling out the tip 9 at a low speed. However, if the former measure is taken, the volume of the tip 9 increases, which makes it difficult to suck the sample m precisely by a desired amount. Further, such an increase in length of the tip 9 leads to an increase in overall size of the pipet device. On the other hand, if the latter measure is taken, the replacement of the tip 9 requires much time, which deteriorates the work efficiency.

DISCLOSURE OF THE INVENTION

The present invention is conceived under the circumstances described above. Therefore, an object of the present invention is to provide a pipet device in which the pipet nozzle is not contaminated with the remaining sample in pulling out the pipet tip from the pipet nozzle.

The pipet device provided according to the present invention includes a pipet nozzle formed with an internal passage and a hollow pipet tip removably attached to the nozzle. The pipet tip is movable between a normal fixed position and a completely detached position relative to the nozzle. The nozzle is formed with an external-air intake. The intake is closed by the tip when the tip is at the normal fixed position. The intake is exposed beyond the tip when the tip is moved from the normal fixed position toward the completely detached position.

Preferably, the nozzle is elongated along an axis, and the intake includes a groove extending along the axis. Alternatively, instead of the groove, the nozzle may be formed with a through-hole communicating with the internal passage of the nozzle.

Preferably, the pipet device according to the present invention further includes an O-ring, and the nozzle is formed with an annular groove for receiving the O-ring.

Preferably, the tip is formed with a fixing groove for engagement with the O-ring.

Preferably, the nozzle includes a lower end to be received in the tip, and the intake is provided between the annular groove and the lower end.

Other features and advantages of the present invention will become clearer from the detailed description given below with reference to the accompanying drawings.

BRIEF DESCRIPTION OF THE DRAWINGS

FIG. 4A is a sectional view illustrating a principal portion of a pipet device according to a second embodiment of the present invention, whereas

FIG. 5A is a sectional view illustrating the basic structure of a prior-art pipet device, whereas

BEST MODE FOR CARRYING OUT THE INVENTION

Preferred embodiments of the present invention will be described below in detail with reference to the accompanying drawings.

Figure 1:
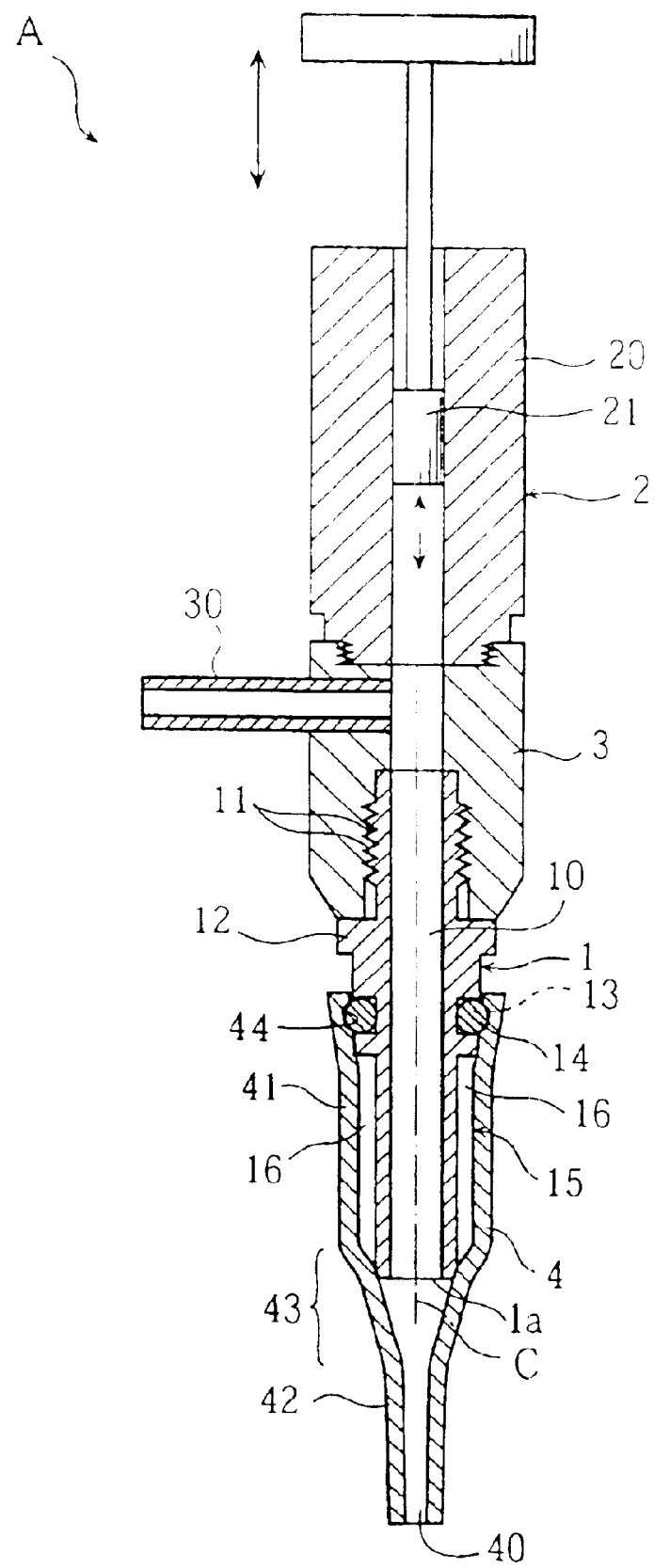
FIG. 1 is a sectional view illustrating a pipet device according to a first embodiment of the present invention.
Figure 2:
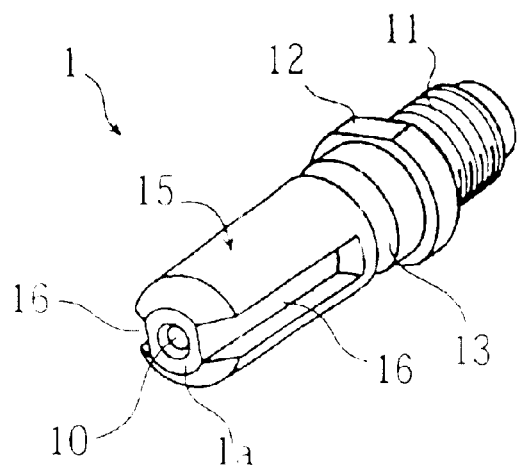
FIG. 2 is a perspective view illustrating a nozzle for use in the pipet device of the first embodiment.
Figure 3:
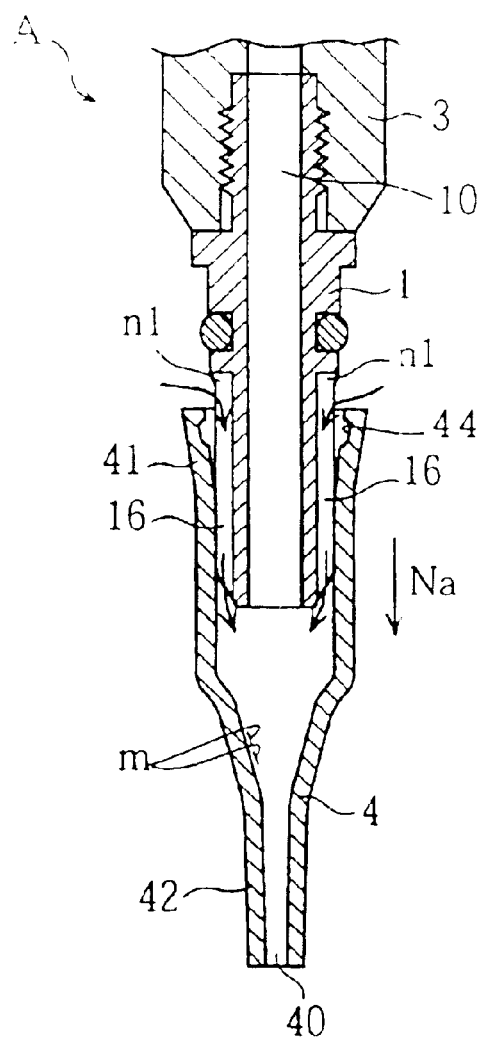
FIG. 3 illustrates the operation of the pipet device of the first embodiment.

FIGS. 1–3 illustrate a pipet device (generally indicated by a reference sign A) according to a first embodiment of the present invention. As clearly shown in FIG. 1, the pipet device A includes a pipet nozzle 1, a syringe pump 2 and a joint tube 3. These structural parts are formed of a corrosion-resistant material such as stainless steel. The pipet device A further includes a pipet tip 4. The tip 4 s removably attached to the nozzle 1.

As shown in FIGS. 1 and 2, the pipet nozzle 1 is generally cylindrical and internally formed with a passage 10 extending along an axis C. The nozzle 1 is upwardly provided with a threaded portion 11 and a flange portion 12 for connection with the joint tube 3. The nozzle 1 is provided, at a longitudinally intermediate portion thereof, with a ring groove 13 for attaching an O-ring 14. The reference numeral 15 indicates the portion of the pipet nozzle 1 between the lower end 1a and the ring groove 13. Hereinafter, this portion is referred to as a "tip-mounting portion".

The tip-mounting portion 15 is formed with two elongate grooves 16 extending along the axis C of the nozzle 1. As clearly shown in FIG. 2, each of the grooves 16 extends from the lower end 1a of the nozzle 1 to the proximity of the ring groove 13.

As shown in FIG. 1, the pipet tip 4 is hollow and includes a first tubular portion 41 having a relatively large diameter and a second tubular portion 42 having a relatively small diameter. The first tubular portion 41 and the second tubular portion 42 are connected to each other via a tapered portion 43. The first tubular portion 41 has an inner circumferential surface formed with an engagement groove 44 for fitting to the O-ring 14. Thus, the first tubular portion 41 can be removably fitted outwardly to the tip-mounting portion 15 of the nozzle 1. The second tubular portion 42 has a lower end formed with an opening 40.

The joint tube 3 functions to connect the nozzle 1 to the syringe pump 2. The joint tube 3 is provided with a branched tube 30. A pressure gauge (not shown) may be attached to the branched tube 30 for measuring the pressure in the nozzle 1. When such pressure measurement is not necessary, the joint tube 3 may not be used. In such a case, the nozzle 1 may directly be connected to the syringe pump 2. Alternatively, as will be described later, the nozzle 1 may be connected to the syringe pump 2 via a flexible hose.

The syringe pump 2 includes a cylinder 20 and a plunger 21 which is reciprocally movable in the cylinder 20. The reciprocating movement of the plunger 21 may be performed utilizing a non-illustrated motor, for example. Alternatively, the plunger 21 may be driven manually. In FIG. 1, by moving the plunger 21 upward, a negative pressure for sucking a sample is generated in the internal passage 10 of the nozzle 1. Conversely, by moving the plunger move downward, a positive pressure for discharging the sample is generated in the internal passage 10 of the nozzle 1.

The pipet device A having the above-described structure is held by a movable holder (not shown) and is therefore movable vertically and horizontally.

The operation of the pipet device A having the above-described structure will be described below.

For performing pipetting, the tip 4 is first fitted outwardly to the tip-mounting portion 15 of the nozzle 1, as shown in FIG. 1. For this purpose, the tip 4 is pushed onto the nozzle 1 until the engagement groove 44 comes into engagement with the O-ring 14 with a click sound. In the description of the present invention, the state in which the engagement groove 44 is kept in proper engagement with the O-ring 14 is described as that the tip 4 is at "the normal fixed position" relative to the nozzle 1.

When the tip 4 is in the normal fixed position defined as above, each of the grooves 16 of the nozzle 1 is covered by the first tubular portion 41 of the tip 4. Therefore, communication is not provided between the inside and the outside of the tip 4 via the grooves 16. Therefore, by moving the syringe pump 2, a sucking pressure (negative pressure) or a discharging pressure (positive pressure) can properly be generated in the tip 4, which enables proper sucking or discharging of the sample into or out of the tip 4 through the opening 40.

Figure 5A:
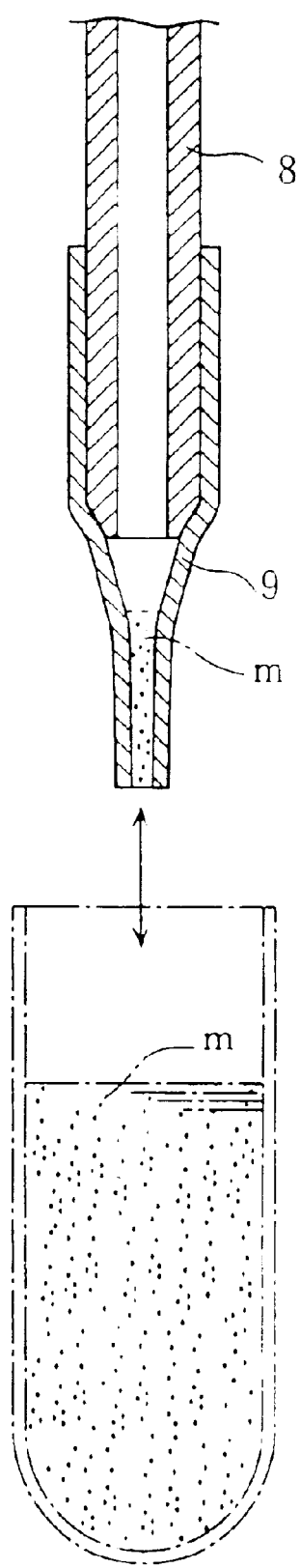
Figure 5B:
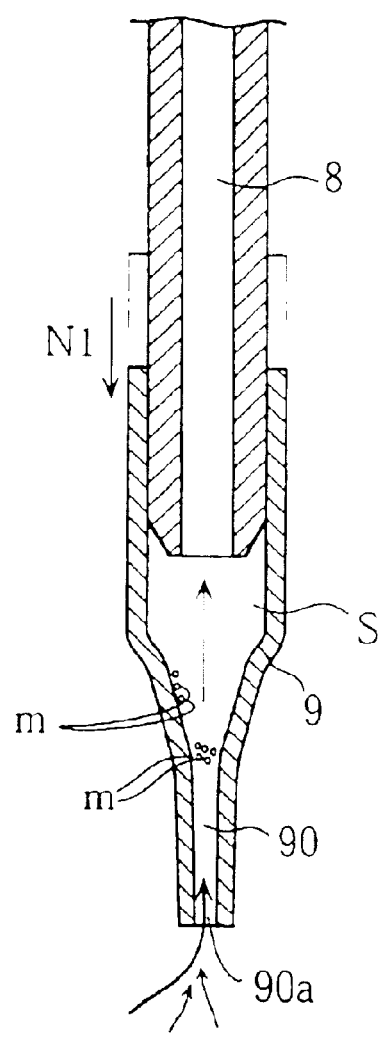
FIG. 5B is a sectional view illustrating a drawback of the prior-art pipet device.

After the pipetting of one sample is completed, the tip 4 is pulled out of the nozzle 1 for replacement with a new tip. As described before, in the prior-art pipet device (FIGS. 5A and 5B), a negative pressure is generated in the tip 9 in pulling out the tip 9 from the nozzle 8 so that the remaining sample contaminates the nozzle 8. However, such a problem does not occur in the pipet device A of the present invention. The reason is as follows.

When the tip 4 is moved in the arrow Na direction in FIG. 3, the upper end portion n1 of each groove 16 shifts to an open state. As a result, the external air flows into the tip 4 through the groove 16, preventing the generation of an undesirable negative pressure. Therefore, even when the tip 4 is pulled out at a high speed, the external air does not flow into the tip 4 through the end opening 40 of the tip 4. Therefore, even when the sample m remains in the tip 4, the sample does not contaminate the nozzle 1. Herein, it is to be noted that the air entering the tip 4 through the grooves 16 flows in the direction to move the remaining sample m away from the nozzle 1. Therefore, the sample m carried by the flowing air does not contaminate the nozzle 1.

In this way, according to the first embodiment of the present invention, it is possible to effectively prevent the remaining sample m from adhering to the nozzle 1 in replacing the tip with a new one. Therefore, even when the pipetting of a second, different sample is performed after the pipetting of a first sample, the first sample does not mix in the second sample.

Further, according to the first embodiment of the present invention, the contamination of the nozzle 1 can be prevented without increasing the length of the tip 4. Therefore, by making the tip 4 appropriately short, the sample can be sucked highly precisely by a small amount.

Figure 4A:
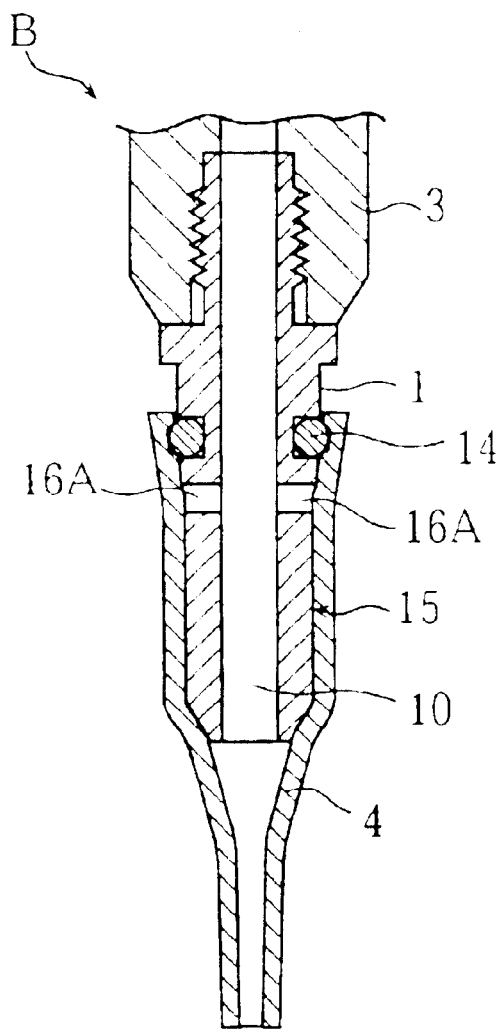
Figure 4B:
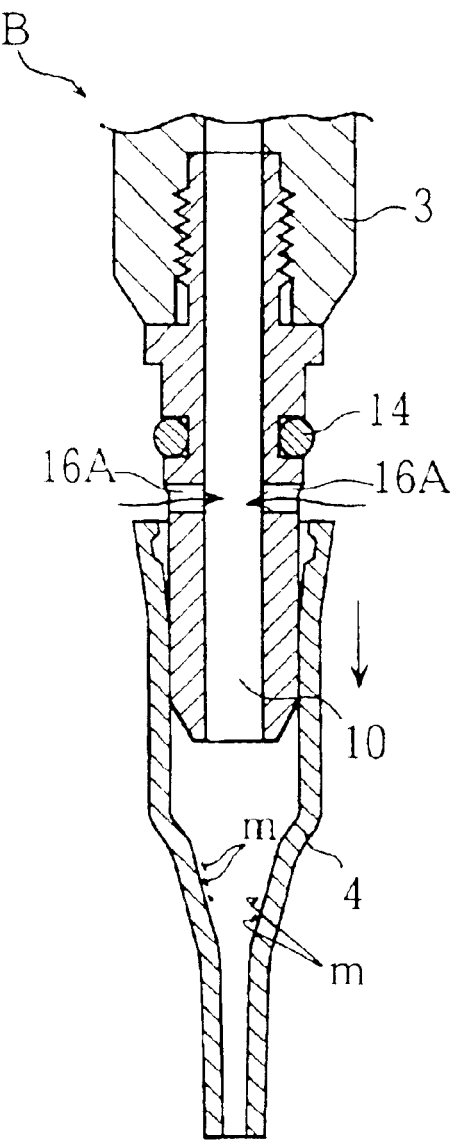
FIG. 4B illustrates the operation of the pipet device of the second embodiment.

FIGS. 4A and 4B illustrate a pipet device (generally indicated by a reference sign B) according to a second embodiment of the present invention. In these figures, the elements which are identical or similar to those of the first embodiment are designated by the same reference signs as those used for the first embodiment. As will be easily understood, the pipet device B of the second embodiment is basically similar to the pipet device A of the first embodiment. Specifically, the pipet device B includes a pipet nozzle 1, a syringe pump (not shown), a joint tube 3 and a pipet tip 4. The nozzle 1 is formed with an internal passage 10. The nozzle 1 further includes a tip-mounting portion 15 for mounting the tip 4.

The pipet device B of the second embodiment differs from the pipet device A of the first embodiment in the following point. Instead of the elongate grooves 16 (See FIG. 2), the tip-mounting portion 15 of the pipet device B is formed with two through-holes 16A. Each of the through-holes 16A penetrates through the wall of the tip-mounting portion 15 for providing communication between the internal passage 10 of the nozzle 1 and the outside.

As shown in FIG. 4A, when the tip 4 is fitted outwardly to the tip-mounting portion 15, the outer opening of each through-hole 16A is closed by tip 4. Therefore, in this state, communication via the through-hole 16A is not provided between the internal passage 10 of the nozzle 1 (and the inside of the tip 4) and the outside. Therefore, a sucking pressure and a discharging pressure necessary for pipetting can properly be generated.

On the other hand, as shown in FIG. 4B, when the tip 4 is began to be pulled out from the nozzle 1, the outer end of each through-hole 16A is exposed to the outside. As a result, the internal passage 10 of the nozzle 10 or the inside of the tip 4 communicates with the outside through the through-hole 16A. Therefore, even when the tip 4 is pulled out from the nozzle 1 at high speed, air does not flow into the tip through the opening 40 of the tip 4 at high speed.

In the two embodiments described above, two external-air intake passages (the elongate grooves 16 in the first embodiment or the through-holes 16A in the second embodiment) are provided. However, the present invention is not limited thereto. According to the present invention, it is only necessary that at least one external-air intake passage is provided. Further, such a passage need not necessarily be provided adjacent to the O-ring 14. According to the present invention, it is only necessary that the external-air intake passage is exposed to the outside when the tip 4 is moved to a certain position between the above-described "normal fixed position" and a "completely detached position" (the position where the tip 4 is completely detached from the nozzle 1). The important point is that the external-air intake passage needs to shift from the closed state by the tip 4 to the opened state before the pressure in the tip 4 becomes excessively low.

As described before, according to the present invention, the nozzle 1 may be connected to the syringe pump 2 via a flexible hose. In such a case, the nozzle alone can be moved by an appropriate moving mechanism with the syringe pump 2 fixed at a predetermined position.

Further, according to the present invention, means other than the syringe pump may be utilized for generating a sucking pressure or a discharging pressure in the tip 4.

The present invention being thus described, it is apparent that the same may be varied in many ways. Such variations should not be regarded as a departure from the spirit and scope of the present invention, and all such modifications as would be obvious to those skilled in the art are intended to be included within the scope of the following claims.

What is claimed is:

1. A pipet device comprising:
   a pipet nozzle formed with an internal passage;
   a hollow pipet tip which is removably attached to the nozzle and which is movable between a first position and a second position relative to the nozzle;
   an annular groove formed on the nozzle;
   an O-ring received in the annular groove; and
   a fixing groove formed on the tip for engagement with the O-ring;
   the nozzle being formed with an external-air intake, the intake being closed by the tip due to engagement of the fixing groove of the tip with the O-ring when the tip is at the first position, the intake being open to outside due to disengagement of the fixing groove of the tip with the O-ring when the tip is moved from the first position to the second position.

2. The pipet device according to claim 1, wherein the nozzle is elongated along an axis, the intake including a groove extending along the axis.

3. The pipet device according to claim 1, wherein the intake comprises a through-hole communicating with the internal passage of the nozzle.

4. The pipet device according to claim 1, wherein the nozzle includes a lower end for fitting in the tip, the intake being provided between the annular groove and the lower end.

5. A pipet device comprising:
   a pipet nozzle formed with an internal passage;
   a hollow pipet tip which is removably attached to the nozzle and which is movable between a normal fixed position and a completely detached position relative to the nozzle;
   an annular grove formed on the nozzle; and
   an O-ring received in the annular groove;
   the nozzle being formed with an external-air intake, the intake being closed by the tip when the tip is at the normal fixed position, the intake being exposed beyond the tip when the tip is moved from the normal fixed position toward the completely detached position;
   wherein the nozzle includes a lower end for fitting in the tip, the intake being provided between the annular groove and the lower end.

6. A pipet device comprising:
   a pipet nozzle formed with an internal passage; and
   a hollow pipet tip which is removably attached to the nozzle and which is movable between a first position and a second position relative to the nozzle;
   the nozzle being formed with an external-air intake formed on the outer surface of the nozzle, the intake being closed by the tip when the tip is at the first position, the intake being open to outside for introducing outside air into the tip when the tip is moved from the first position to the second position while the tip is held attached to the nozzle.

* * * * *